(12) United States Patent
Priatna

(10) Patent No.: US 10,588,523 B2
(45) Date of Patent: Mar. 17, 2020

(54) 4D FLOW MEASUREMENTS OF THE HEPATIC VASCULATURES WITH TWO-DIMENSIONAL EXCITATION

(71) Applicant: Siemens Healthcare GmbH, Erlangen (DE)

(72) Inventor: Agus Priatna, Ballwin, MO (US)

(73) Assignee: Siemens Healthcare GmbH, Erlangen (DE)

( * ) Notice: Subject to any disclaimer, the term of this patent is extended or adjusted under 35 U.S.C. 154(b) by 1007 days.

(21) Appl. No.: 15/099,814

(22) Filed: Apr. 15, 2016

(65) Prior Publication Data

US 2017/0296072 A1   Oct. 19, 2017

(51) Int. Cl.
| | |
|---|---|
| A61B 5/05 | (2006.01) |
| A61B 5/026 | (2006.01) |
| A61B 5/00 | (2006.01) |
| G01R 33/483 | (2006.01) |
| G01R 33/563 | (2006.01) |
| G01R 33/561 | (2006.01) |
| G01R 33/567 | (2006.01) |
| G01R 33/54 | (2006.01) |

(52) U.S. Cl.
CPC .......... *A61B 5/0263* (2013.01); *A61B 5/004* (2013.01); *A61B 5/4244* (2013.01); *A61B 5/742* (2013.01); *A61B 5/748* (2013.01); *G01R 33/4836* (2013.01); *G01R 33/5612* (2013.01); *G01R 33/5635* (2013.01); *G01R 33/5676* (2013.01); *G01R 33/56316* (2013.01); *A61B 2576/02* (2013.01); *G01R 33/546* (2013.01)

(58) Field of Classification Search
None
See application file for complete search history.

(56) References Cited

U.S. PATENT DOCUMENTS

| | | | |
|---|---|---|---|
| 8,643,365 B2 | 2/2014 | Harder et al. | |
| 2013/0127460 A1* | 5/2013 | Beck | G01N 24/08 324/309 |
| 2014/0210469 A1* | 7/2014 | Cheng | G01R 33/56509 324/309 |
| 2014/0296702 A1* | 10/2014 | Griswold | G01R 33/3614 600/416 |
| 2014/0334702 A1* | 11/2014 | El Fakhri | G06T 11/005 382/131 |
| 2016/0054417 A1* | 2/2016 | Kuhara | A61B 5/055 324/309 |

* cited by examiner

Primary Examiner — Joel F Brutus

(57) ABSTRACT

A computer-implemented method of visualizing blood flow through a patient using magnetic resonance imaging (MRI) includes receiving an image of the portal venous system of the patient's liver at a full field of view. A reduced field of view is defined which encompasses the portal venous system of the patient's liver and excludes extraneous anatomy in the full field of view. A navigator area is defined in the full field of view and outside of the reduced field of view. Transmit channels are used to selectively excite the reduced field of view and the navigator area throughout a cardiac cycle of the patient. Measurement data is acquired in response to the selective excitation. The acquired data is used to generate time-resolved 3D datasets. Additionally, a 3D visualization of blood flow though the portal venous system is generated based on the time-resolved 3D datasets.

20 Claims, 7 Drawing Sheets

4D FLOW MEASUREMENTS OF THE HEPATIC VASCULATURES WITH TWO-DIMENSIONAL EXCITATION

TECHNOLOGY FIELD

The present invention relates generally to methods, systems, and apparatuses for measuring 4D Flow of hepatic vasculatures with two-dimensional Magnetic Resonance Imaging (MRI) excitation. The disclosed techniques may be applied to, for example, enhance resolution and reduce scan time in various hepatic imaging applications.

BACKGROUND

Time-resolved three-directional three-dimensional (3D) phase-contrast MRI, often referred to as "4D Flow MRI" or simply "4D Flow," is a powerful tool for the noninvasive measurement of blood flow in the cardiovascular system. The 4D Flow technique obtains anatomical and three-directional velocity information, for each voxel within a 3D-volume and at each measured time point of the cardiac cycle.

4D Flow has traditionally been used for imaging of the cardiac structures such as the aorta, cranial arteries, carotid arteries, etc. Recently, 4D Flow applications have been extended for the measurements of the portal venous flow in the liver for patients with portal hypertension for surgeries such as transvenous intrahepatic portosystemic surgery. The current method for this liver application, however, is not effective as the technique excites a large field of view with low resolution that covers regions that are not of interest, thus can extend the scan time. Furthermore, the use of traditional 90-180 cross section navigator is cumbersome for this application and can interfere with the signal of the imaging volume.

SUMMARY

Embodiments of the present invention address and overcome one or more of the above shortcomings and drawbacks, by providing methods, systems, and apparatuses related to a 4D Flow technique for measuring the flow of hepatic vasculatures with two-dimensional MM excitation. Briefly, parallel transmit is used in combination with a "zoom" function which allows the acquired field of view (FOV) to be reduced and targeted such that the amount of measurement data acquired during each acquisition is minimized.

According to some embodiments, a computer-implemented method of visualizing blood flow through a patient using magnetic resonance imaging (MM) includes receiving an image of the portal venous system of the patient's liver at a full field of view. A reduced field of view is defined which encompasses the portal venous system of the patient's liver and excludes extraneous anatomy in the full field of view. A navigator area is defined in the full field of view and outside of the reduced field of view. The reduced field of view and the navigator area may be defined, for example, based on user-selection of the respective regions in a graphical user interface (e.g., by placing a box over the selected region). Transmit channels are used to selectively excite the reduced field of view and the navigator area throughout a cardiac cycle of the patient. The selective excitation may be performed using one or more specific pulse sequences. For example, the navigator area may be selectively excited using a plurality of 2D spin echo (SE) RF pulses or a plurality of 2D gradient echo (GE) RF pulses. Measurement data is acquired in response to the selective excitation. The acquired data is used to generate time-resolved 3D datasets. Additionally, a 3D visualization of blood flow though the portal venous system is generated based on the time-resolved 3D datasets based on the measurement data. In some embodiments, one or more hemodynamic measurements at a location within the portal venous system may be quantified based on the plurality of time-resolved 3D datasets The aforementioned method may have additional features, refinements, or other variations in different embodiments. For example, prior to selectively exciting the reduced field of view and the navigator area throughout the cardiac cycle, a pre-processing step may be performed to correct for eddy currents present in the portal venous system. Additionally (or alternatively), a blood pool agent may be administered to the patient such that it enhances signal to noise of blood in the portal venous system in the 3D visualization of blood flow. In some embodiments, a lung-spleen boundary position is identified based on the plurality of time-resolved 3D datasets and one or more of the time-resolved 3D datasets may be discarded if the lung-spleen boundary position is not within a range of predetermined values.

According to other embodiments, an article of manufacture for visualizing blood flow through a patient using MRI comprises a non-transitory, tangible computer-readable medium holding computer-executable instructions for performing the aforementioned method, with or without the additional features set out above.

According to other embodiments, a system for acquiring 4D blood flow data using MM comprises an imaging computer and an MM scanner. The imaging computer is configured to receive an image of the portal venous system of a patient's liver at a full field of view, define a reduced field of view which encompasses the portal venous system of the patient's liver and excludes extraneous anatomy in the full field of view, and further define a navigator area in the full field of view and outside of the reduced field of view. The MM scanner is configured to selectively excite the reduced field of view and the navigator area throughout a cardiac cycle of the patient, wherein velocity is encoded along all three spatial dimensions of the reduced field of view throughout the cardiac cycle. Additionally, the MM scanner acquires measurement data throughout the cardiac cycle in response to the selective excitation of the reduced field of view and the navigator area.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to measuring 4D Flow of hepatic vasculatures with two-dimensional excitation. The techniques described herein utilize a parallel transmit architecture that allows 2D excitation with short RF pulse duration on the 3D phase contrast sequence. The 2D RF pulse only excites a small field of view for the region of interest, and in this case only the portal venous system of the liver. This provides various benefits including, without limitation, higher image resolution and shorter acquisition time in comparison to conventional techniques.

Figure 1:
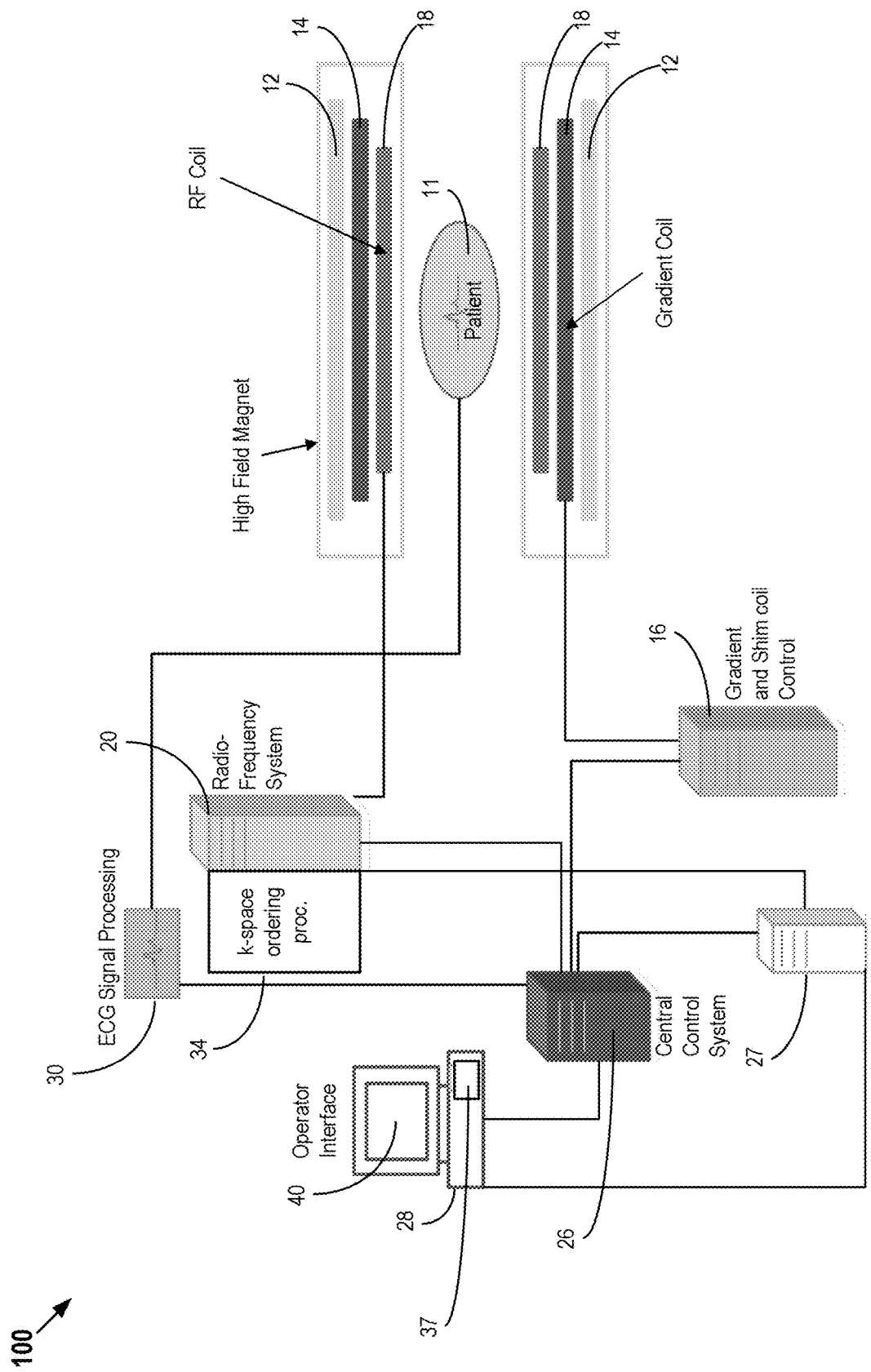
FIG. 1 shows a system for ordering acquisition of frequency domain components representing magnetic resonance image data for storage in a k-space storage array, as used by some embodiments of the present invention.

FIG. 1 shows a system 100 for ordering acquisition of frequency domain components representing MRI data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further, radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components is acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques may be used for reconstruction. For example, as described in greater detail below, an optimization algorithm is applied to iteratively solve a cost function which results in the reconstructed image.

The system 100 described in FIG. 1 can be adapted to provide a parallel transmit architecture that allows 2D excitation with short RF pulse duration on the 3D phase contrast sequence. This parallel transmit architecture comprises two components: configuration of the transmission hardware to support parallel excitation of the subject and a "zoom" feature which facilitates the imaging of field of view (FOV) which is focused on the anatomical features of interest. The advantages of the local excitation on the 3D phase contrast sequence of the portal venous system include, for example, allowing higher resolution by increasing the matrix size (or base resolution) for a given small field of view, allowing shorter acquisition as the Ky and Kx steps are shorter than the conventional method, and allowing a better navigator pulse that does not interfere with the imaging signal. Additionally, the navigator pulse can also be designed with the parallel transmit system to use a short duration 2D navigator RF pulse for better navigator.

Parallel transmission (also referred to as "parallel excitation") refers to the transmission of a plurality of individual radio-frequency pulse trains in parallel over the different, independent radio-frequency transmit channels. Thus, the transmit field is deconstructed into multiple regions which each are controlled by a separate transmit channel. This configuration creates spatial degrees of freedom that allow the spatial information in the array to be exploited in the excitation process. In, turn, this results in higher image quality and faster scan times compared to systems that do not utilize parallel transmit.

The zoom feature uses selective excitation to limit the scope of the acquisition volume, adapting the FOV—with regard to its dimensions in the plane (perpendicular to the slice thickness direction)—to the structures of interest. This speeds up the scan and improves the image quality in the selected zoom area. Techniques for limiting the FOV are discussed generally, in U.S. patent application Ser. No. 14/484,576, filed Sep. 12, 2013 and entitled "Method and magnetic resonance apparatus to generate a spatially selective excitation," the entirety of which is incorporated herein by reference. Any of these techniques may be adapted to limit acquisition to the hepatic vasculatures in the patient. For example, in one embodiment, an initial image of the hepatic vasculatures is acquired and used to define one or more slices. Conceptually, each slice is virtually bounded at the top and bottom by two flat planes. A respective partial region is selected which encompasses the hepatic vasculatures, while excluding other regions which are not of interest to the clinical application. MR measurement signals are acquired from each corresponding slice such that the acquired measurement signals originate only from the respective partial region of the corresponding slice. Then, one or more MR images of the hepatic vasculatures are created based on the acquired MR measurement signals. Note that, acquisition is limited to signals from the limited partial region, the measurement time is reduced.

Figure 2A:
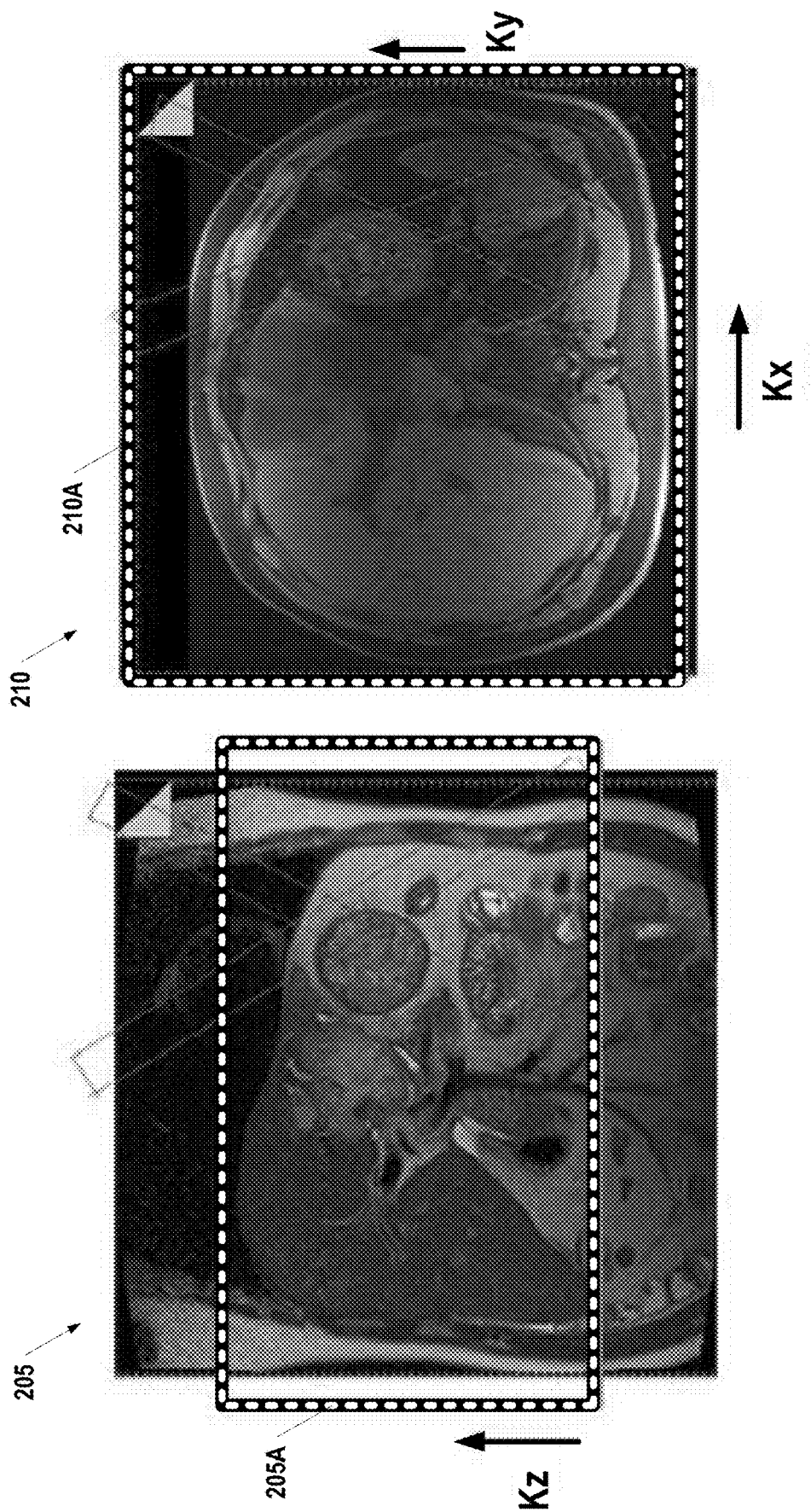
FIG. 2A images provide two different views of the liver-spleen anatomy of a patient.
Figure 2B:
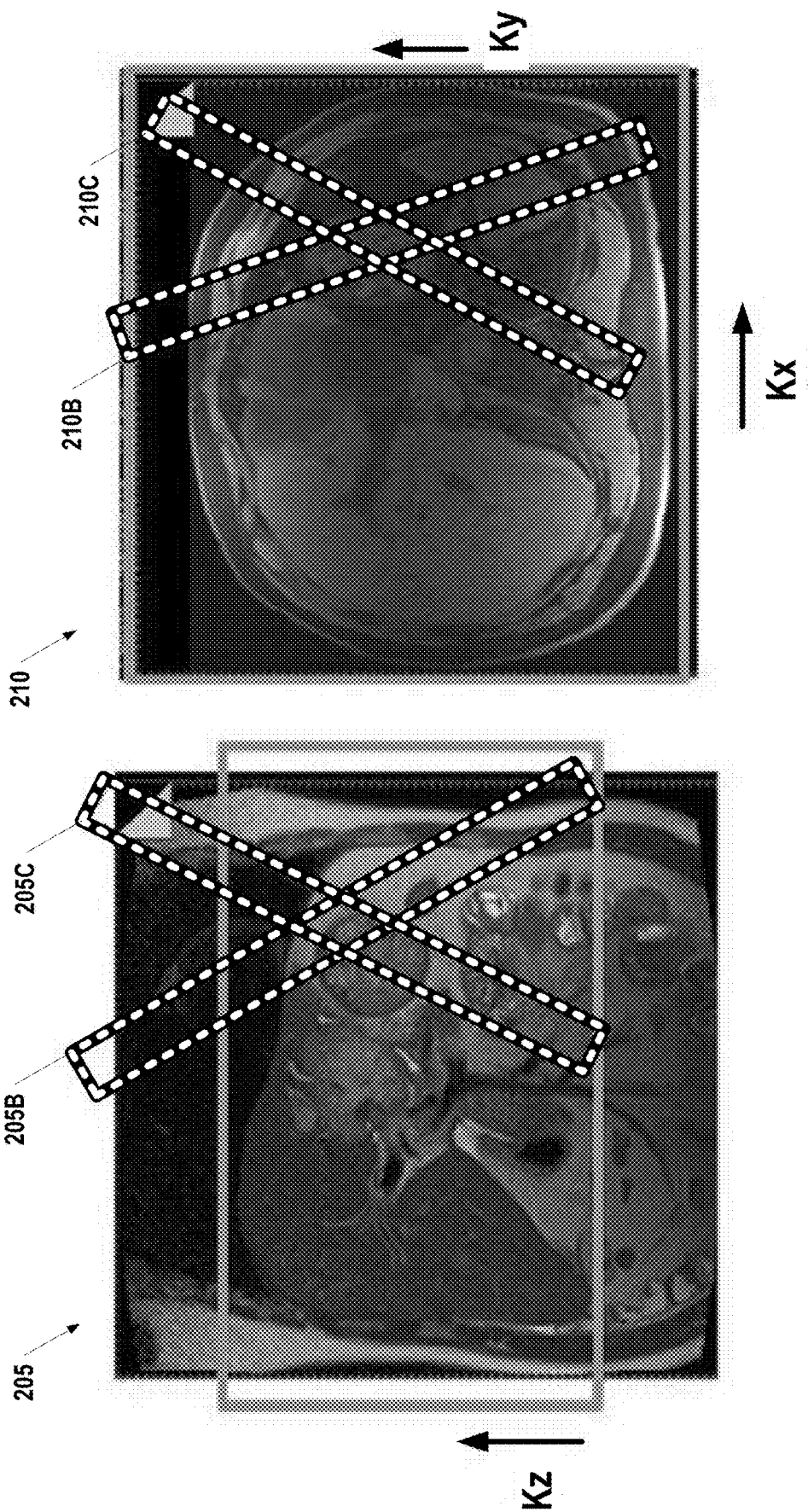
FIG. 2B provides an illustration of navigators used in the images shown in FIG. 2A.
Figure 3A:
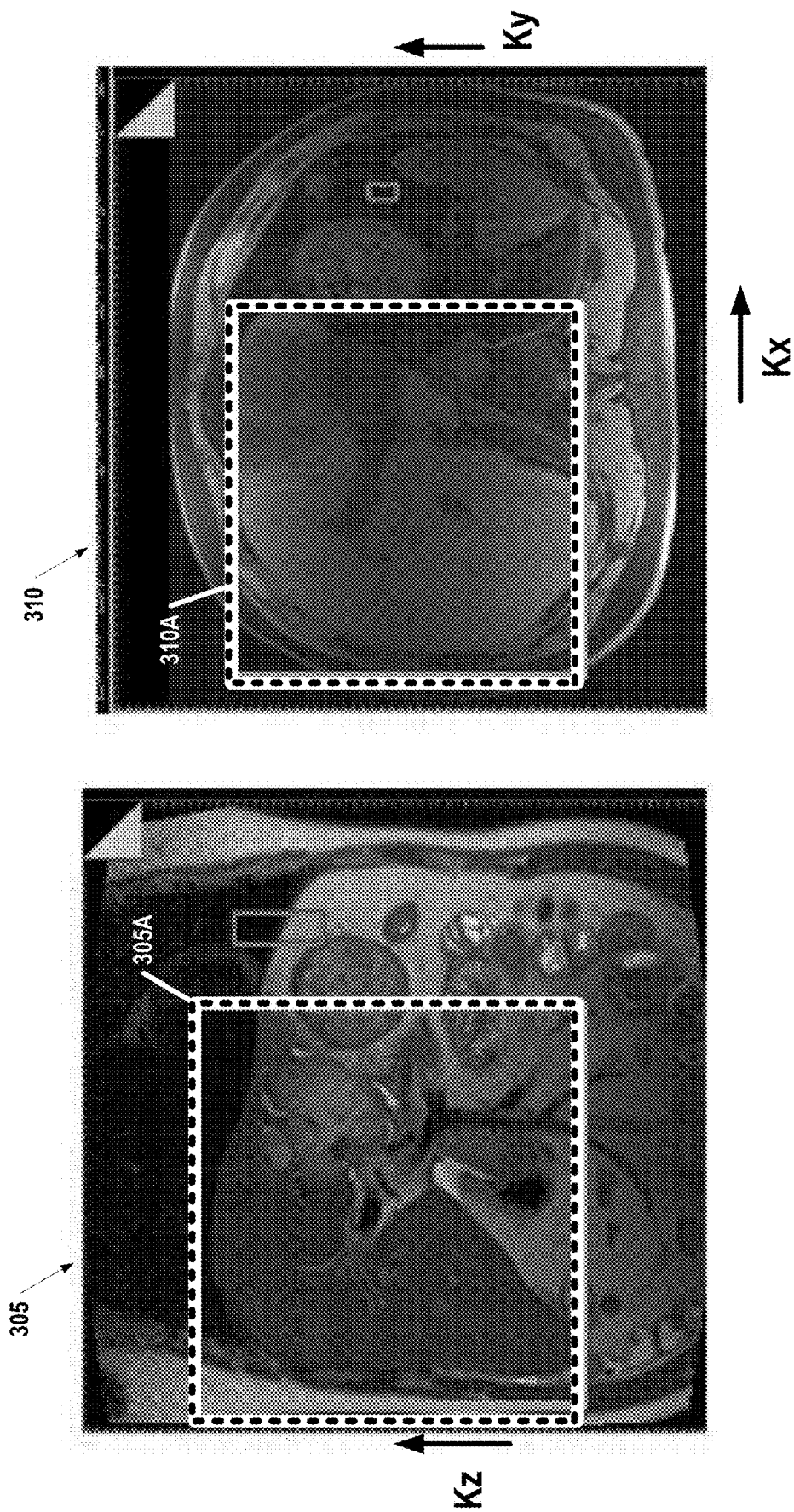
FIG. 3A shows an acquisition similar to FIG. 2A using the parallel transmit technology, according to some embodiments of the present invention.

FIGS. 2A, 2B, 3A, and 3B provide images which illustrate how the parallel architecture described herein may be applied to the imaging of the hepatic vasculatures. Starting with FIG. 2A images 205 and 210 provide two different views of the liver-spleen anatomy of a patient. In these figures the dotted-lined boxes 205A and 210A represent the FOV acquired with conventional systems. Note that, in addition to the hepatic vasculatures, additional anatomy is imaged which is irrelevant to the flow measurement for the purpose of transvenous intrahepatic portosystemic surgery. FIG. 3A shows a similar acquisition using the parallel transmit technology described herein. The two images 305 and 310 shown in FIG. 3A are similar to the views presented in FIG. 2A; however, note that the corresponding FOV of each image (305A, 310A) is significantly smaller. Because less measurement data is acquired, the overall scan time is reduced.

FIG. 2B provides an illustration of navigators used in the images 205 and 210. The term "navigator," as used herein, refers to RF tracking pulses used to detect physiologic motion in a patient. By measuring the phase shift of navigator echoes, the position of anatomical structures can be monitored during image acquisition. In FIG. 2B these navigators are represented by the dotted-lined boxes 205B, 205C, 210B, 210C on each image 205, 210; however, it should be noted, that the dotted lines are only used for emphasis and, in actual images, a more subtle visual representation is used. For each image, pencil-shaped volume is placed across a diaphragm in two positions corresponding to two points in a respiratory cycle. Thus, in image 205, these two positions correspond to volumes 205B and 205C, respectively. Similarly, in image 210, the two positions correspond to volumes 210B and 210C, respectively. For each image 205, 210, the cross-section of the volume defining the navigator is the intersection of the two pencil-shaped bands in the axial plane. The length of the navigator is depicted in the coronal plane.

In some embodiments, the navigators correspond to motion detection via one dimensional Prospective Acquisition Correction (1D-PACE). The 1D-PACE method of respiratory motion detection is relatively fast and typically performed within 30 ms for minimizing the effects of breathing motion in cardiac imaging examinations. For this purpose, image data representing the pencil-shaped volume comprising a single line of data that crosses the diaphragm is acquired. The volume is interactively placed in such a way that the position of the diaphragm can be calculated and used for motion correction in real time.

One by-product of image acquisition with navigators is that the magnetization is saturated in the navigation volumes causing dark lines to be present in the acquired images. An alternative to 1D-PACE is two dimensional Prospective Acquisition Correction (2D-PACE). In 2D-PACE, an image is acquired by means of a low-resolution gradient echo sequence featuring a low flip angle, for example. This ensures that dark lines in the image are avoided. However, the time used to acquire an image for 2D-PACE can be significantly longer than 1D-PACE (e.g., 100 ms for 2D-PACE v. 30 ms for 1D-PACE). While this additional time may be acceptable for some image acquisition scenarios, for parallel transmit applications utilizing zoom, the additional time may offset some of the timing advantages provided by limiting the overall field of view.

Figure 3B:
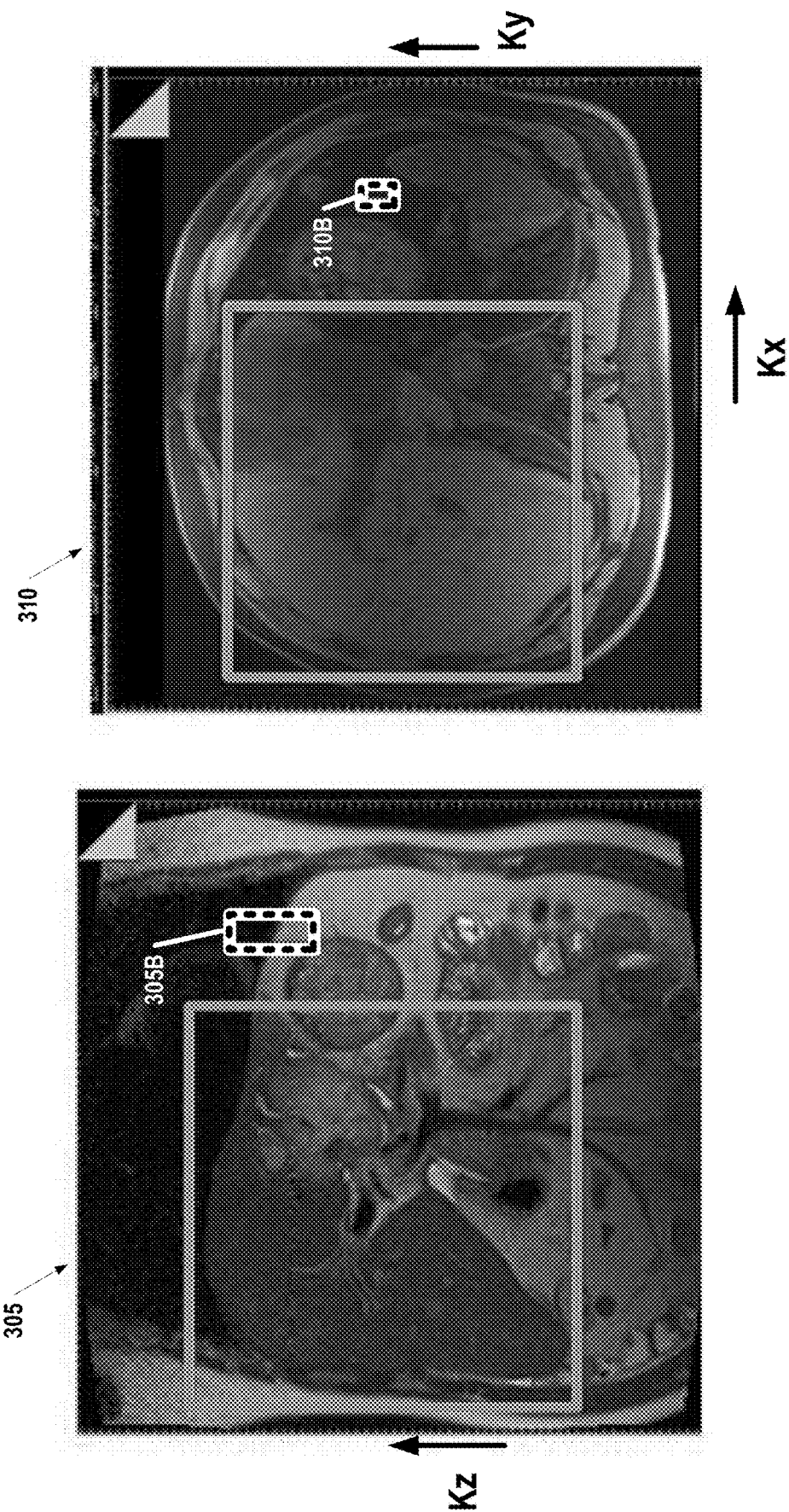
FIG. 3B shows a technique for navigator placement that utilizes parallel transmit with zoom, according to some embodiments of the present invention.

FIG. 3B shows an alternative technique for navigator placement that utilizes parallel transmit with zoom. Here, navigator volumes in images 305, 310 are represented by boxes 305B and 310B. Similar to the technique described above with reference to FIG. 3A, the user can place the box selectively over the smallest region which would provide the desired information (i.e., diaphragm movement) within the field of view. For example, in image 305, the user places box 305B across the diaphragm on the 2D image for detection of the diaphragm position. Approximately half the box covers the lungs, while the other half covers the liver. Once placed, these boxes may be acquired with the parallel transmit techniques described above. Note that, because the navigator volumes 305B, 310B are outside of the field of view of the main image volume (i.e., volumes 305A, 310A in FIG. 3A), there is no risk acquisition of the navigator volume will result dark lines in the final image reconstructed from the main image volume.

Figure 4:
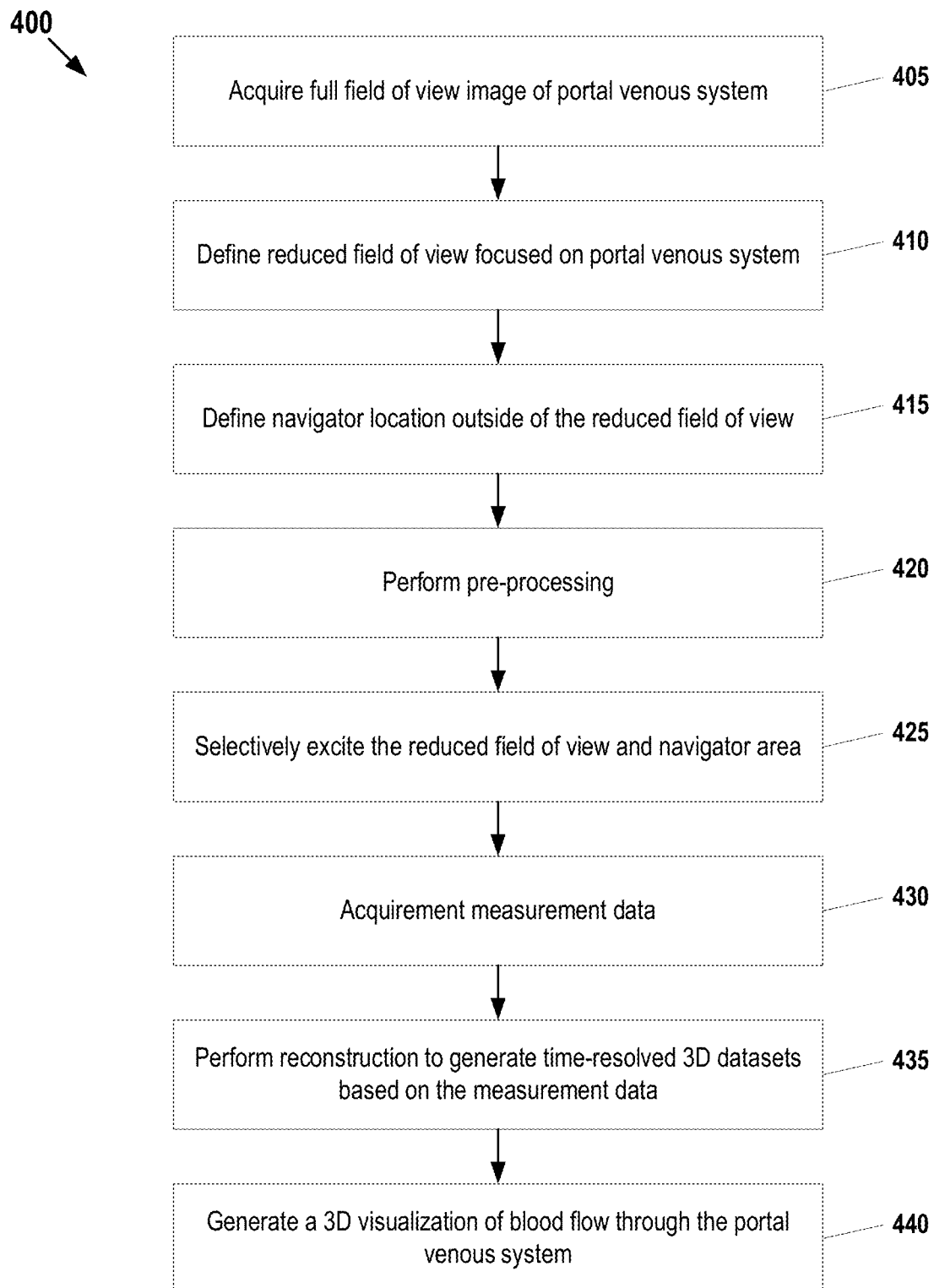
FIG. 4 illustrates a process for visualizing blood flow through the portal venous system of a patient using MRI, according to some embodiments.

FIG. 4 illustrates a process 400 for visualizing blood flow through the portal venous system a patient using MRI, according to some embodiments. At step 405, an image of the portal venous system of the patient's liver is acquired at a full field of view using an MM system (e.g., system 100 in FIG. 1). In general any technique known in the art may be used in acquiring the image at 405. Next, at step 410 the image is used to define a reduced field of view which encompasses the portal venous system of the patient's liver and excludes extraneous anatomy in the full field of view. This reduced field of view may be defined using automated detection and segmentation of the area around the portal venous system. Alternatively, the user may manually select the reduced field of view. For example, in one embodiment, a graphical user interface (GUI) is presented to the user with the full field of view image. The user can then select the reduced field of view by clicking and dragging a box over the desired region of the image. In other embodiments, semi-automated techniques may be used where user input is used in conjunction with automated techniques. At step 415, a navigator area in the full field of view and outside of the reduced field of view is defined. The navigator area may be selected using one or more of the techniques described above with respect to step 410 (e.g., automated detection, user manual selection of the region, etc.).

At step 420, one or more pre-processing steps are performed. For example, a blood pool agent or alternate contrast agent may be applied to the patient such that it will enhance signal to noise of blood in the portal venous system during later visualization (described below). Additionally, one or more correction methods may be applied during step 420 such as noise correction, eddy current correction, and/or anti-aliasing.

Continuing with reference to FIG. 4, at 425, a plurality of transmit channels included in the MM system are used to selectively excite the reduced field of view and the navigator area throughout a cardiac cycle of the patient. During this selective excitation, velocity is encoded along all three spatial dimensions of the reduced field of view throughout the patient's cardiac cycle. In general, the selective excitation may be performed using any 4D Flow pulse sequence known in the art. Additionally, within the pulse sequence, the pulses used for acquisition of navigator data may vary from embodiment to embodiment. For example, in some embodiments, the navigator area is selectively excited using 2D spin echo (SE) RF pulses. In other embodiments, the navigator area is excited using 2D gradient echo (GE) RF pulses. In response to the selective excitation performed at step 425, measurement data covering the reduced field of view and navigator area is acquired at step 430 throughout the cardiac cycle. The general steps involved with acquiring data using an MM system are discussed above with respect to FIG. 1.

At step 435, a reconstruction process is applied to the measurement data to generate time-resolved 3D datasets. In some embodiments, the navigator data is used to discard images where blurring occurs due to patient respiration or other motion. For example, in one embodiment, the position of the patient's lung-spleen boundary position is identified based on the plurality of time-resolved 3D datasets (e.g., using a classifier or other automated techniques), and the datasets are discarded if the interface position is not within a range of predetermined values corresponding to the anatomical characteristics of the patient. These values may be determined, for example, at the time of scanning based on measurements of the patent or, alternatively, generic values from previous studies may be employed. At step 440, the time-resolved 3D datasets are used to generate a 3D visualization of blood flow though the portal venous system of the patient's liver. This visualization may then be presented on display for review by the clinician.

Aside from the visual presentation of blood flow, in some embodiments, hemodynamic measurements may be quantified at a location within the portal venous system based on the time-resolved 3D datasets. These hemodynamic measures may include, for example, pressure differences, pulse wave velocity, turbulent kinetic energy, a measure of wall shear stress.

Figure 5:
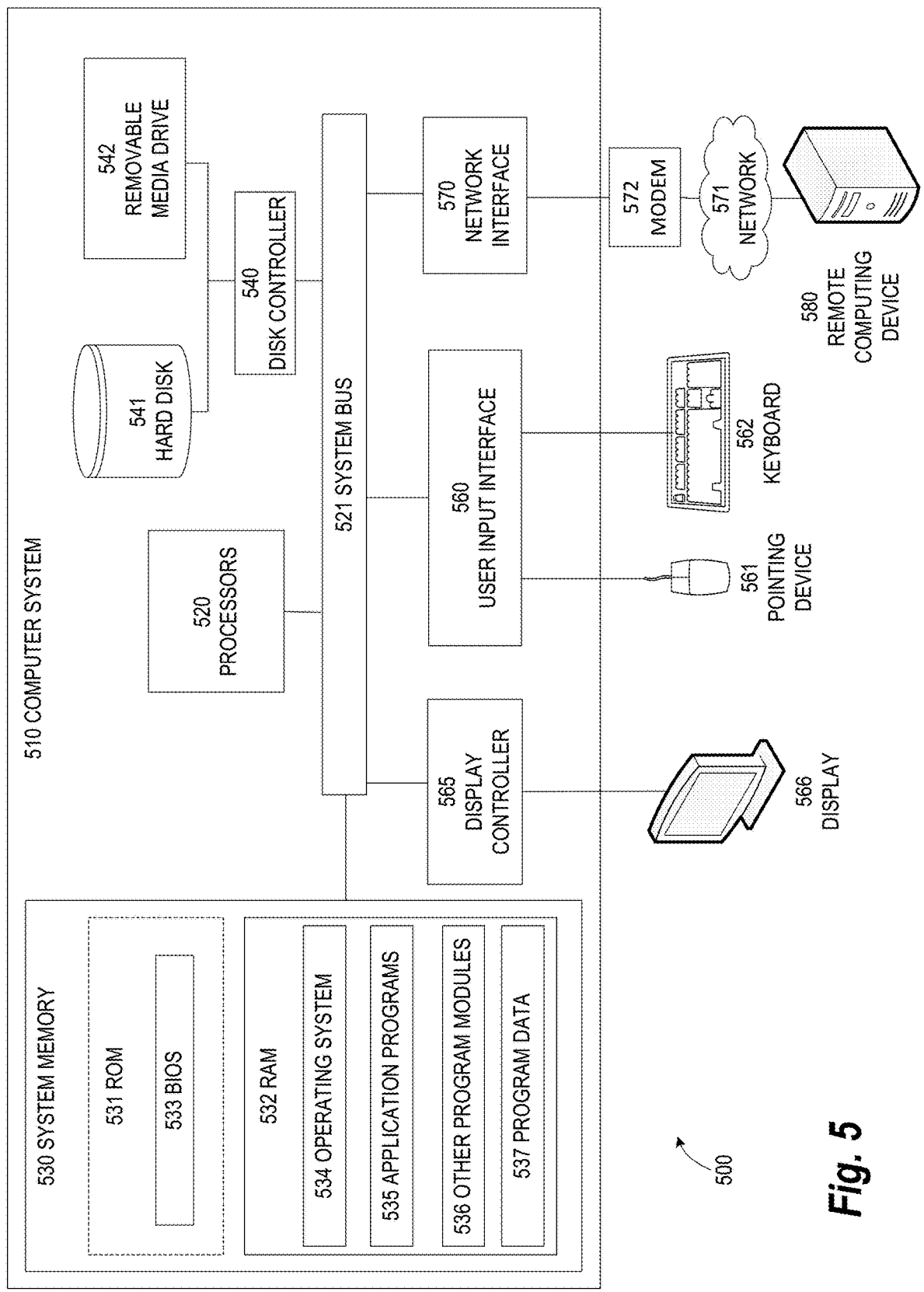
FIG. 5 illustrates an exemplary computing environment within which embodiments of the invention may be implemented.

FIG. 5 illustrates an exemplary computing environment 500 within which embodiments of the invention may be implemented. For example, this computing environment 500 may be used to implement the process 400 described in FIG. 4 and/or one or more of the components illustrated in the system 100 of FIG. 1. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system (BIOS) 533 containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only.

Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 55 U.S.C. 112, sixth paragraph, unless the element is expressly recited using the phrase "means for."

I claim:

1. A computer-implemented method of visualizing blood flow through a patient using magnetic resonance imaging (MM), the method comprising:
   receiving, by a computer system, an image of the portal venous system of the patient's liver at a full field of view;
   defining, by the computer system, a reduced field of view which encompasses the portal venous system of the patient's liver and excludes extraneous anatomy in the full field of view;
   defining, by the computer system, a navigator area in the full field of view and outside of the reduced field of view;
   using a plurality of transmit channels to selectively excite the reduced field of view and the navigator area throughout a cardiac cycle of the patient, wherein velocity is encoded along all three spatial dimensions of the reduced field of view throughout the cardiac cycle;
   acquiring measurement data throughout the cardiac cycle in response to the selective excitation of the reduced field of view and the navigator area;
   generating, by the computer system, a plurality of time-resolved 3D datasets based on the measurement data; and
   generating, by the computer system, a 3D visualization of blood flow though the portal venous system of the patient's liver based on the plurality of time-resolved 3D datasets based on the measurement data.

2. The computer-implemented method of claim 1, further comprising:
   quantifying one or more hemodynamic measurements at a location within the portal venous system based on the plurality of time-resolved 3D datasets.

3. The computer-implemented method of claim 1, further comprising:
   prior to selectively exciting the reduced field of view and the navigator area throughout the cardiac cycle, performing a pre-processing step comprising a correction for eddy currents present in the portal venous system.

4. The computer-implemented method of claim 1, further comprising:
   prior to selectively exciting the reduced field of view and the navigator area throughout the cardiac cycle, administering a blood pool agent to the patient such that it enhances signal to noise of blood in the portal venous system in the 3D visualization of blood flow.

5. The computer-implemented method of claim 1, wherein the reduced field of view is defined by a user selection of an area of the full field of view.

6. The computer-implemented method of claim 5, further comprising:
   displaying the full field of view in an interactive graphical user interface (GUI),
   wherein the area of the full field of view is designated by a box placed by a user over the area.

7. The computer-implemented method of claim 1, wherein the navigator area is defined by a user selection of a navigator area of the full field of view.

8. The computer-implemented method of claim 7, further comprising:
   displaying the full field of view in an interactive GUI;
   wherein the navigator area of the full field of view is designated by a box placed by a user over the navigator area.

9. The computer-implemented method of claim 1, further comprising:
   identifying a lung-spleen boundary position based on the plurality of time-resolved 3D datasets; and
   discarding the plurality of time-resolved 3D datasets if the lung-spleen boundary position is not within a range of predetermined values.

10. The computer-implemented method of claim 1, wherein the navigator area is selectively excited using a plurality of 2D spin echo (SE) RF pulses.

11. The computer-implemented method of claim 1, wherein the navigator area is selectively excited using a plurality of 2D gradient echo (GE) RF pulses.

12. An article of manufacture for visualizing blood flow through a patient using Mill, the article of manufacture comprising a non-transitory, tangible computer-readable medium holding computer-executable instructions for performing a method comprising
   receiving an image of the portal venous system of the patient's liver at a full field of view;
   defining a reduced field of view which encompasses the portal venous system of the patient's liver and excludes extraneous anatomy in the full field of view;
   defining a navigator area in the full field of view and outside of the reduced field of view;
   providing instructions to an MM scanner which cause the MM scanner to selectively excite the reduced field of view and the navigator area throughout a cardiac cycle of the patient, wherein velocity is encoded along all three spatial dimensions of the reduced field of view throughout the cardiac cycle,
   receiving measurement data throughout the cardiac cycle in response to providing the instructions to the MRI scanner;
   generating a plurality of time-resolved 3D datasets based on the measurement data; and
   generating a 3D visualization of blood flow though the portal venous system of the patient's liver based on the plurality of time-resolved 3D datasets based on the measurement data.

13. The article of manufacture of claim 12, wherein the method further comprises:
   quantifying one or more hemodynamic measurements at a location within the portal venous system based on the plurality of time-resolved 3D datasets.

14. The article of manufacture of claim 12, wherein the method further comprises:
   prior to selectively exciting the reduced field of view and the navigator area throughout the cardiac cycle, performing a pre-processing step comprising a correction for eddy currents present in the portal venous system.

15. The article of manufacture of claim 12, wherein the method further comprises:
   receiving a user designation of an area of the full field of view; and
   using the user designation to define the reduced field of view.

16. The article of manufacture of claim 15, wherein the method further comprises
    displaying the full field of view in an interactive graphical user interface (GUI),
    wherein the area of the full field of view is designated by a box placed by a user over the area.

17. The article of manufacture of claim 12, wherein the method further comprises:
    receiving a user designation of a navigator area of the full field of view; and
    using the user designation to define the navigator area.

18. The article of manufacture of claim 17, wherein the method further comprises displaying the full field of view in an interactive GUI;
    wherein the navigator area of the full field of view is designated by a box placed by a user over the navigator area.

19. The article of manufacture of claim 12, wherein the method further comprises:
    identifying a lung-spleen boundary position based on the plurality of time-resolved 3D datasets; and
    discarding the plurality of time-resolved 3D datasets if the lung-spleen boundary position is not within a range of predetermined values.

20. A system for acquiring 4D blood flow data using MRI, the system comprising:
    an imaging computer configured to:
        receive an image of the portal venous system of a patient's liver at a full field of view;
        define a reduced field of view which encompasses the portal venous system of the patient's liver and excludes extraneous anatomy in the full field of view;
        define a navigator area in the full field of view and outside of the reduced field of view; and
    an MRI scanner configured to:
        selectively excite the reduced field of view and the navigator area throughout a cardiac cycle of the patient, wherein velocity is encoded along all three spatial dimensions of the reduced field of view throughout the cardiac cycle,
        acquire measurement data throughout the cardiac cycle in response to the selective excitation of the reduced field of view and the navigator area.

* * * * *